United States Patent [19]

Townsend et al.

[11] Patent Number: 4,899,735
[45] Date of Patent: Feb. 13, 1990

[54] TORSION BAR SPLINT FOR FOREARM

[75] Inventors: Kim R. Townsend, Garner, N.C.; Susan G. Bledsoe, New Lenox, Ill.; Michael Heidenreich, Lafayette; Michael H. Voelz, Battleground, both of Ind.

[73] Assignee: Bissell Health Care Corporation, Grand Rapids, Mich.

[21] Appl. No.: 281,030

[22] Filed: Dec. 7, 1988

[51] Int. Cl.$^4$ ............................................. A61F 5/04
[52] U.S. Cl. .................................. 128/87 R; 128/88; 128/77; 128/25 R; 272/67
[58] Field of Search ................... 128/25 R, 26, 77, 83, 128/87 R, 88, 92 Z; 272/67

[56] References Cited

U.S. PATENT DOCUMENTS

| 1,639,815 | 8/1927 | Siebrandt . | |
| 1,961,118 | 5/1934 | Ettinger | 128/88 |
| 2,310,566 | 2/1943 | Anderson | 128/84 |
| 2,415,288 | 2/1947 | Jordan | 128/88 |
| 2,661,000 | 12/1953 | Gaxeley et al. | 128/88 |
| 3,698,389 | 10/1972 | Guedel | 128/77 |
| 4,259,949 | 4/1981 | Axelsson | 128/77 |
| 4,384,571 | 5/1983 | Nuzzo et al. | 128/77 |
| 4,392,649 | 7/1983 | Chapman | 272/67 |
| 4,538,600 | 9/1985 | Hepburn | 128/88 |
| 4,651,719 | 3/1987 | Funk et al. | 128/25 |
| 4,677,971 | 7/1987 | Lindemann | 128/87 |
| 4,691,698 | 9/1987 | Bremer | 128/80 |
| 4,716,889 | 1/1988 | Saringer | 128/25 |

OTHER PUBLICATIONS

Article "Spring Splint to Supinate or Pronte the Hand" by Sterling Bunnell, MD–from an Orthopedic Journal–published around 1948.
Article "Splints" taken from J B Lippencott, Bunnell Surgery of the Hand–1947.
Article "A Rational Approach for the Recognition & Treatment of Colles' Fracture" by E. R. Weber—published vol. 3, No. 1, *Hand Clinics* (2/87).
Article "Fractures & Traumatic Conditions of the Wrist" by Gary K. Frykman & Elvert F. Nelson published in *Rehab of the Hand*, 1947.
Article "Splints Acting on the Wrist & Forearm", Chapter 10, *Hand Splinting Principles & Methods*, 2nd Ed. 1988.

Primary Examiner—Robert A. Hafer
Assistant Examiner—Lynda M. Cofsky
Attorney, Agent, or Firm—Price, Heneveld, Cooper, DeWitt & Litton

[57] ABSTRACT

A wrist and forearm range-of-motion exercising device includes a first member adapted to be secured to a portion of the hand, a second member adapted to be secured to a portion of the upper arm and interconnecting means, including a one-way clutch, for interconnecting the members and providing unidirectional rotation along the axis of interconnection. The device retains the forearm in the position to which it is rotated under the control of the patient or as assisted by a therapist. A tension release device may be actuated to allow the forearm to return to the relaxed position.

13 Claims, 2 Drawing Sheets

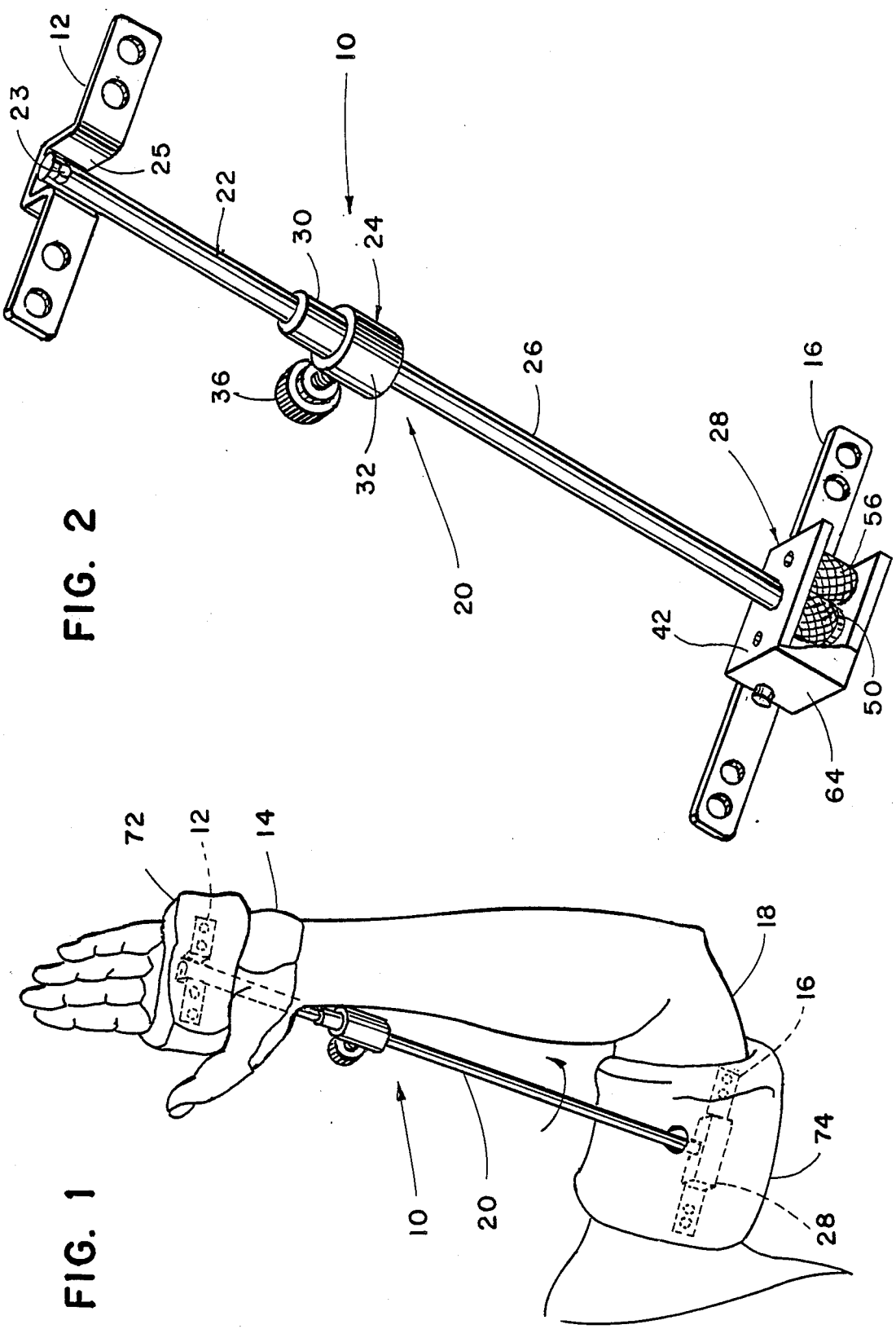

TORSION BAR SPLINT FOR FOREARM

BACKGROUND OF THE INVENTION

This invention relates to a splint for the distal radioulnar joint and in particular to such a splint which provides mobilization of the joint.

Following fractures, neurological injury and related traumatic conditions of the distal radioulnar joint, or wrist, the wrist is typically immobilized until the injured tissue has healed enough to provide some degree of stability. Such immobilization tends to cause a loss of motion in the wrist of varying degree depending upon the severity of the injury and age of the patient. To overcome the stiffness in the radioulnar joint and to promote full use of the wrist, active wrist range of motion exercises, including pronation and supination are necessary.

Devices to assist in regaining pronation and supination motion at the distal radioulnar joint, also known as forearm rotation, have been developed. One such known device includes a member attached to the hand and another member attached to a portion of the upper arm. Resilient means extend between such members to provide a resistance against which the patient exerts a force by rotating the forearm. The spring force in the resilient member provides resistance to the rotation of the forearm, the amount of resistance increasing with the degree of rotation. Another such known device actively provides gradual rotation to the forearm through its range of motion while the elbow is bent 90° at the patient's side.

Such prior art devices are useful in the advanced stages of recovery after trauma to the wrist but find limited application immediately after immobilization is discontinued due to the tendency for such devices to cause pain. The resulting increase in pain as the patient attempts an ever greater degree of mobilization tends to discourage attempts at yet further mobilization. Other difficulties experienced by such prior art devices, that the present invention is intended to overcome, include the inability of the patient to apply, or mount the device without assistance using only the noninjured hand. Thus, such devices have been limited to use in a clinical environment and have not found application in the patient's home. Additionally, such devices have not provided means that may be adjusted by the patient for increasing or decreasing the degree of resistance to the patient's mobilization efforts.

Active assisted range-of-motion exercises require the assistance of a trained therapist. Further, unless the elbow is flexed 90° and adducted close to the body during the pronation-supination exercises, the patient may inadvertently perform shoulder abduction rather than wrist pronation-supination. Improperly perform exercises may lead to permanent loss of motion in the radioulnar joint with a resulting reduction of functional abilities.

It is an object of the present invention to provide a range of motion exercising device and method for use in mobilizing the distal radioulnar joint following immobilization that overcomes the difficulties of the prior art devices and methods.

SUMMARY OF THE INVENTION

A radioulnar mobilization splint according to the invention includes a first member adapted to be secured to a portion of the hand, a second member adapted to be secured to a portion of the upper arm and interconnecting means extending between the members, along an axis, for interconnecting the members. The interconnecting means includes one-way clutch means for allowing relative rotation along the axis in one direction while opposing rotation in the opposite direction. In this manner, the patient mobilizes the distal radioulnar joint by rotating the wrist in the direction allowed by the one-way clutch using pain as a guide for the patient to pronate or supinate as far as can be tolerated. The mobilization splint guides the movement of the wrist and forearm in the pronation-supination axes, limiting the shoulder abduction and other compensatory motions which mimick wrist pronation and supination.

These and other related objects, advantages and features of this invention will become apparent upon review of the following specification in conjunction with the drawings.

BRIEF DESCRIPTION OF THE DRAWINGS

FIG. 1 is a front perspective view of a mobilization splint according to the invention shown in its intended use on the forearm of a patient;

FIG. 2 is a perspective view of a mobilization splint according to the invention.

DESCRIPTION OF THE PREFERRED EMBODIMENT

Figure 3:
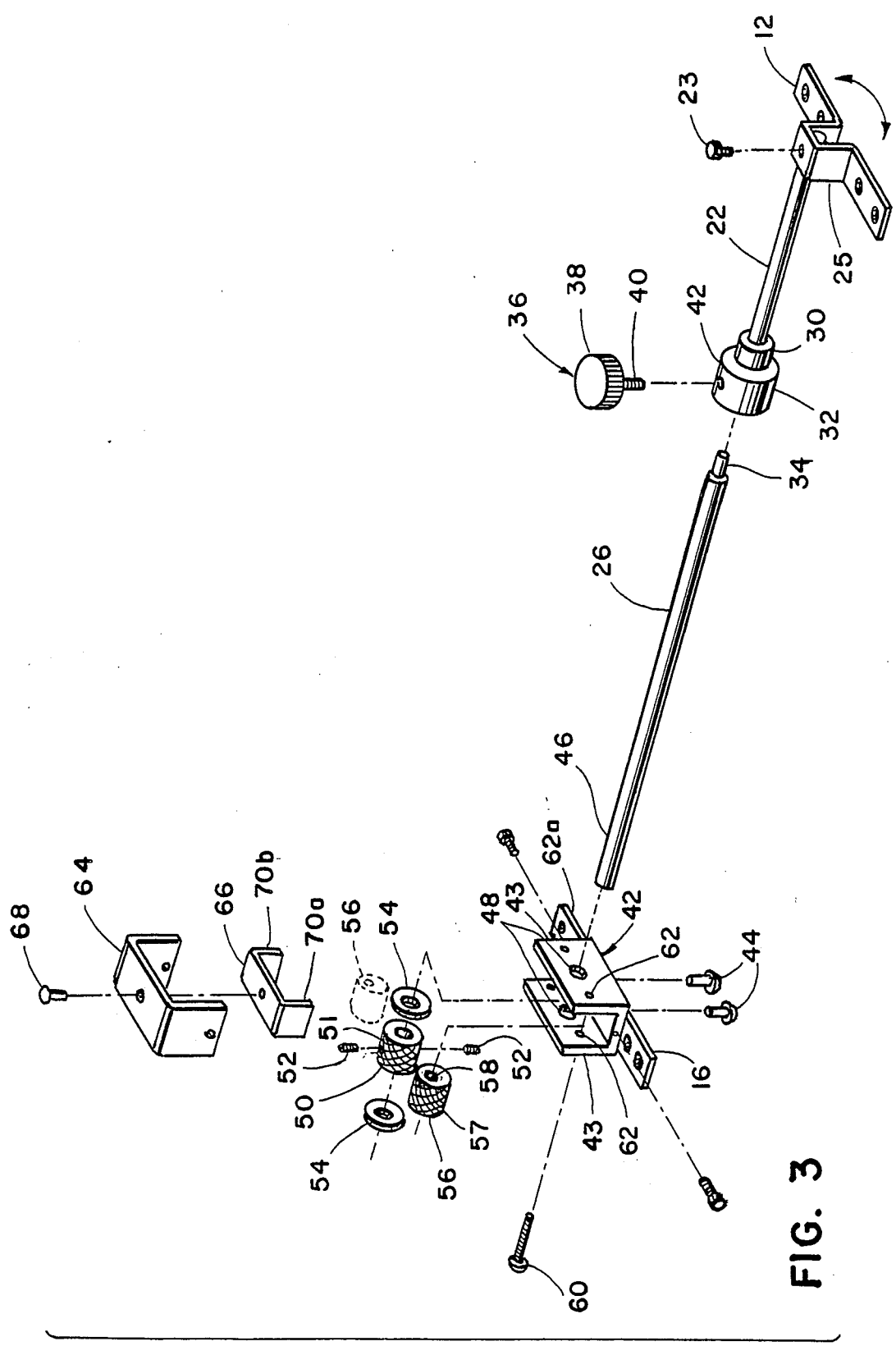
FIG. 3 is an exploded view of the mobilization splint in FIG. 2 illustrating the relationship of the components.

Referring now specifically to the drawings, and the illustrative embodiments depicted therein, a radioulnar mobilization splint, generally shown at 10, includes a first member 12 configured for attachment to the posterior surface of the patient's hand 14, a second member 16 configured for attachment to a portion of the patient's upper arm 18 and means generally shown at 20 for interconnecting the first and second members. Interconnecting means 20 includes a first rod 22 extending between first member 12 and a coupling member 24 and a second rod 26 extending between coupling member 24 and a one-way clutch 28 which is attached to second member 16.

Coupling member 24 includes a shoulder 30 rigidly attached to rod 22 and a sleeve 32 integrally formed with shoulder 30 and having a central bore (not shown) for receipt of a knurled portion 34 of rod 26 (FIG. 3). A clamping screw 36, including a knob 38 joined to threaded rod 40, is threadably received in a threaded opening 42 extending through the wall of sleeve 32. With knurled portion 34 in the bore of sleeve 32, and with clamping screw 36 rotated inwardly, the end of threaded portion 40 thereof engages the knurled surface of portion 34 to retain first and second rods 22 and 26 in nonrotatable engagement. When screw 36 is loosened, relative rotation between rods 22 and 26 is facilitated. First member 12 is pivotally connected to first rod 22, for pivoting about an axis perpendicular to the axis of the connecting means, by pivot means 23. First member 12 includes an offset central portion 25 that is joined to rod 22, allowing only limited relative pivoting of member 12 with respect to rod 22.

One-way clutch 28 includes a housing 42 affixed to second member 16 by fasteners 44. Housing 42 is U-shaped, including a pair of upstanding walls 43. A cover member 64 spans walls 43 and encloses the housing. An end portion 46 of rod 26 is journaled in housing 42 by aligned openings 48 in walls 43. A first traction member 50 is positioned between walls 43 inside of housing 42 and is nonrotatably attached to end portion 46 of rod 26 by set screws 52. A pair of washers 54 are positioned between opposite end portions of traction member 50 and walls 43. Traction member 50 is cylindrical and includes a knurled cylindrical surface 51.

A second traction member 56 includes a bore 58 extending axially therethrough and positioned offset from the central axis of the traction member to define an eccentric wheel. A shaft 60 extends between aligned openings 62 in walls 43 and through bore 58 to mount second traction member 56. Shaft 60 is positioned parallel to first traction member 50 and spaced from knurled surface 57 less than half the diameter of member 56. Second traction member 56 includes a cylindrical knurled traction surface 57. U-shaped cover member 64 includes a U-shaped biasing member 66 attached on an inner surface thereof by a fastener 68. Biasing member 66 includes converging tongues 70a and 70b, one of which engages surface 57 of eccentric traction member 56 to bias it into contact with knurled surface 51 of first traction member 50.

With one tongue 70 biasing eccentric second traction member 56 into contact with the traction surface of first traction member 50, surfaces 51 and 57 will wedge together when traction member 50 is rotated in one direction. This prevents further rotation of traction member 50 in this direction. Because second rod 26 is nonrotatably attached to traction member 50, traction rod 26 is not capable of rotating in the direction that causes a wedging action between traction members 50 and 56. Conversely, when traction member 50 and attached rod 26 are rotated in the opposite direction, surfaces 51 and 57 slide with respect to each other to allow rotation of member 50 and rod 26 in the second direction. Thus, it is seen, that a one-way clutch is provided to allow relative rotation between second rod 26 and second member 16 along the axis of connecting means 20 in a first direction and resisting relative rotation between rod 26 and member 16 in the opposite direction. Because first rod 22 and first member 12 are nonrotatably joined to second rod 26 when clamping screw 36 is engaged, clutch 28 provides a one-way clutch between members 12 and 16.

A second set of aligned openings 62a in housing 42 accommodate an alternative mounting of second traction member 56 in the phantom position illustrated in FIG. 3 to provide one-way clutch action that is opposite to that provided when the eccentric traction member is mounted as described above. Thus, by a simple mechanical modification of removing cover 64 and repositioning second traction member 56, mobilization splint 10 may be readily converted from a right-hand to a left-hand application. In the illustrated embodiment, the components of mobilization splint 10 are made of original stainless steel, with the exception of the traction members, which are made of aluminum. In this manner, mobilization splint 10 is capable of being autoclavable and reusable.

With reference now to FIG. 1, radioulnar mobilization splint 10 is used by attaching first member 12 to the posterior surface of hand 14 by a low temperature splint or cast 72. Second member 16 is affixed in relationship to upper arm 18 by a low temperature splint or cast 74, with second member 16 parallel to the humerus bone. With clamping screw 36 tightened, coupling member 24 will be retaining rods 22 and 26 nonrotatable with respect to each other. First member 12 may be rotated along the axis of connecting means 20 in the direction provided by one-way clutch 28. This provides true pronation-supination movement of the forearm and may be accomplished under the control of the wrist muscles, by the use of the patient's other hand or by the assistance of a therapist.

As hand 14 is further pronated or supinated, one-way clutch 28 retains the wrist in the furthest extent of its range-of-motion. The patient is encouraged to extend the range-of-motion as tolerated. When it is desired to release the distal radioulnar joint to return to the relaxed position, clamping screw 36 of coupling member 24 is loosened to allow relative rotation between rods 22 and 26. Once the forearm is relaxed in the supinated or pronated position, clamping screw 36 is again tightened to reconnect members 22 and 26 for subsequent range-of-motion exercises. Rods 22 and 26 are rigid and provide extension support for hand 14, and thus the distal radioulnar joint, during the range-of-motion exercise. Pivot means 23 accommodates the palmar arch during the range-of-motion exercises.

The invention provides a range-of-motion exercising device and method for the wrist which includes support for the distal radioulnar joint while assisting pronation-supination motion. Once attached to the patient, the exerciser may be utilized by the patient without the immediate supervision of a trained therapist and can be worn several hours a day, which decreases the number of required therapy sessions.

Because the mobilization splint according to the invention does not provide spring force resistance to the patient's efforts, the patient is encouraged to continually extend the range of motion with increased use of the device. The one-way clutch retains the forearm in the farthest mobilized position attained by the patient to further relieve the stiffness in the distal radioulnar joint. This prolonged stretch gradually improves mobility in the joint. The torsion-release means may be operated by the patient to release the torsion force established by the patient to allow the wrist to return to the relaxed position.

A device according to the present invention is compact and unobtrusive when utilized by a patient and is easily fitted and adjusted by the patient without assistance. The use of outriggers and other cumbersome devices in the prior art is eliminated. Changes and modifications in the specifically described embodiments can be carried out without departing from the principles of the invention, which is intended to be limited only by the scope of the appended claims, as interpreted according to the principles of patent law including the doctrine of equivalents.

The embodiments of the invention in which an exclusive property or privilege is claimed are defined as follows:

1. A radioulnar mobilization splint comprising:
  a first member adapted to be secured to a portion of the hand;
  a second member adapted to be secured to a portion of the arm proximal the proximal radioulnar joint;
  interconnecting means extending between said members along an axis for interconnecting said members; and
  clutch means associated with said interconnecting means for allowing relative rotation between said members along said axis in one direction away from a set orientation and substantially preventing relative rotation between said members along said axis in the direction opposite said one direction and toward said set orientation, whereby progressive unidirectional rotation along said axis is accommodated between the hand to which said first member is coupled and the arm to which said second member is coupled.

2. The splint in claim 1 further including torsion release means associated with said interconnecting means and selectively operable for allowing relative rotation between said members along said axis in the direction opposite said one direction, said torsion release means being operable by a patient to release torsional forces developed between said hand and said arm.

3. The splint in claim 2 in which said interconnecting means includes a first rod extending between one of said members and said release means and a second rod extending between said release means and said clutch means, said clutch means being attached to the other one of said members.

4. The splint in claim 3 in which said rods are rigid.

5. The splint in claim 3 further including pivot means connecting said first member to the respective one of said rods for accommodating limited pivotal movement of said first member perpendicular said axis.

6. The splint in claim 3 in which said first member is adapted to be secured to the posterior surface of the hand.

7. The splint in claim 6 in which said second member is adapted to be secured parallel to the humerus.

8. The splint in claim 3 in which said clutch means includes a housing, means for rotatably journaling said second rod through a wall of said housing, a first traction member associated with said second rod in a manner to be rotatable therewith, a second traction member mounted in said housing and wedging means responsive to the direction of rotation of said first traction member for selectively wedging said traction members together.

9. A radioulnar mobilization splint comprising:
a first member adapted to be secured to a portion of the hand;
a second member adapted to be secured to a portion of the arm proximal the proximal radioulnar joint;
interconnecting means extending between said members along an axis for interconnecting said members;
clutch means associated with said interconnecting means for allowing relative rotation between said members along said axis in one direction and resisting relative rotation between said members along said axis in the direction opposite said one direction, whereby progressive unidirectional rotation along said axis is accommodated between the hand to which said first member is coupled and the arm to which said second member is coupled;
torsion release means associated with said interconnecting means and selectively operable for allowing relative rotation between said members along said axis in the direction opposite said one direction, said torsion release means being operable by a patient to release torsional forces developed between said hand and said arm;
said interconnecting means including a first rod extending between one of said members and said release means and a second rod extending between said release means and said clutch means, said clutch means being attached to the other one of said members; and
said clutch means including a housing, means for rotatably journaling said second rod through a wall of said housing, a first traction member associated with said second rod in a manner to be rotatable therewith, a second traction member mounted in said housing and wedging means responsive to the direction of rotation of said first traction member for selectively wedging said traction members together, said first traction member including a first cylindrical traction surface coaxial with its axis of rotation, said second traction member including a second cylindrical surface parallel said first surface and means defining a bore through said second traction member parallel said second surface, said bore being offset from the central axis of said second traction member defining an eccentric wheel, and said clutch means further including a shaft extending through said bore and mounted in said housing parallel to said first traction surface and spaced therefrom less than half the diameter of said second traction member.

10. A radioulnar mobilization spring comprising:
a first member adapted to be secured to a portion of the hand;
a second member adapted to be secured to a portion of the arm proximal the proximal radioulnar joint;
interconnecting means extending between said members along an axis for interconnecting said members;
clutch means associated with said interconnecting means for allowing relative rotation between said members along said axis in one direction and resisting relative rotation between said members along said axis in the direction opposite said one direction, whereby progressive unidirectional rotation along said axis is accommodated between the hand to which said first member is coupled and the arm to which said second member is coupled;
torsion release means associated with said interconnecting means and selectively operable for allowing relative rotation between said members along said axis in the direction opposite said one direction, said torsion release means being operable by a patient to release torsional forces developed between said hand and said arm;
said interconnecting means including a first rod extending between one of said members and said release means and a second rod extending between said release means and said clutch means, said clutch means being attached to the other one of said members; and
said clutch means including a housing, means for rotatably journaling said second rod through a wall of said housing, a first traction member associated with said second rod in a manner to be rotatable therewith, a second traction member mounted in said housing and wedging means responsive to the direction of rotation of said first traction member for selectively wedging said traction members together, said wedging means including means for changing the direction of rotation to which said wedging means is responsive for wedging said traction members together, whereby said splint may be modified for use with either the right or the left hand.

11. A method of providing range of motion therapy to the distal radioulnar joint including the steps of:

providing a mobilization splint having a first member adapted to be secured to a portion of the hand, a second member adapted to be secured to a portion of the arm and interconnecting means extending between said members along an axis for interconnecting said members, said interconnecting means including one-way clutch means for allowing relative rotation along said axis in one direction away from a set orientation but not in the direction opposite said one direction and toward said set orientation;

securing said first member to said hand and said second member to the corresponding arm proximal of the proximal radioulnar joint;

rotating said hand along said axis as tolerance permits, whereby said mobilization splint will retain the hand at the maximum extent of rotation.

12. The method in claim 11 in which said splint further includes torsion release means selectively operable for allowing relative rotation along said axis in said direction opposite said one direction and said method further including the step of operating said release means after said step of rotating.

13. The method in claim 11 including securing said first member to the posterior surface of the hand and said second member parallel to the humerus.

* * * * *